United States Patent
Govari et al.

(10) Patent No.: US 12,263,121 B2
(45) Date of Patent: *Apr. 1, 2025

(54) CONTROLLING VIBRATION PATTERNS OF A PHACOEMULSIFICATION NEEDLE

(71) Applicant: JOHNSON & JOHNSON SURGICAL VISION, INC., Irvine, CA (US)

(72) Inventors: Assaf Govari, Haifa (IL); Vadim Gliner, Haifa (IL)

(73) Assignee: Johnson & Johnson Surgical Vision, Inc., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/630,323

(22) Filed: Apr. 9, 2024

(65) Prior Publication Data
US 2024/0252352 A1 Aug. 1, 2024

Related U.S. Application Data

(62) Division of application No. 17/090,484, filed on Nov. 5, 2020, now Pat. No. 11,969,381.

(51) Int. Cl.
*A61F 9/007* (2006.01)
*A61B 17/00* (2006.01)
*B06B 1/02* (2006.01)

(52) U.S. Cl.
CPC ........ *A61F 9/00745* (2013.01); *B06B 1/0284* (2013.01); *A61B 2017/00402* (2013.01); *A61B 2217/005* (2013.01); *A61B 2217/007* (2013.01); *B06B 2201/55* (2013.01); *B06B 2201/76* (2013.01)

(58) Field of Classification Search
CPC .............. A61F 9/00745; B06B 1/0284; B06B 2201/55; B06B 2201/76; A61B 2017/00402; A61B 2217/005; A61B 2217/007
See application file for complete search history.

(56) References Cited

U.S. PATENT DOCUMENTS

| | | |
|---|---|---|
| 5,843,109 A | 12/1998 | Mehta et al. |
| 8,784,357 B2 | 7/2014 | Zhou |
| 10,485,699 B2 | 11/2019 | Steen et al. |
| 2002/0099400 A1 | 7/2002 | Wolf |
| 2003/0045887 A1 | 3/2003 | Sakurai |
| 2005/0020990 A1 | 1/2005 | Akahoshi |
| 2006/0052758 A1 | 3/2006 | Dewey |

(Continued)

FOREIGN PATENT DOCUMENTS

| | | |
|---|---|---|
| CN | 111557784 A | 8/2022 |
| JP | H0796000 A | 4/1995 |
| WO | 2013154925 A2 | 10/2013 |

*Primary Examiner* — Phong Son H Dang
*Assistant Examiner* — Andrew P. Restaino (57) ABSTRACT

A system includes a needle, an actuator assembly and a generator. The needle is configured to be vibrated so as to emulsify a lens of an eye. The actuator assembly, includes a first actuator, a second actuator and a third actuator, which are distributed around a longitudinal axis of the needle and are configured to vibrate along the longitudinal axis in response to a first driving signal, a second driving signal and a third driving signal, respectively. The generator is configured to generate the first driving signal, the second driving signal and the third driving signal, so as to vibrate the needle in accordance with a predefined pattern.

18 Claims, 3 Drawing Sheets

Generate a first driving signal, a second driving signal and a third driving signal for vibrating a needle in a vibration pattern specified for emulsifying a lens of an eye ~110

Apply (i) the first driving signal to a first actuator, (ii) the second driving signal to a second actuator, and (iii) the third driving signal to a third actuator, the first, second and third actuators are distributed around a longitudinal axis of the needle for deflecting the needle from the longitudinal axis in a first direction, a second direction and a third direction, respectively ~112

(56) References Cited

U.S. PATENT DOCUMENTS

2007/0249942 A1    10/2007   Salehi et al.
2009/0005712 A1    1/2009   Raney
2009/0225388 A1    9/2009   Zaifrani et al.
2010/0094321 A1    4/2010   Akahoshi et al.
2015/0335483 A1    11/2015   Chon
2017/0027750 A1    2/2017   Wiley

CONTROLLING VIBRATION PATTERNS OF A PHACOEMULSIFICATION NEEDLE

CROSS-REFERENCE TO RELATED APPLICATIONS

This application is a divisional of U.S. application Ser. No. 17/090,484, filed Nov. 5, 2020, which is currently allowed. The entire contents of the aforementioned application are incorporated herein by reference in its entirety.

FIELD OF THE INVENTION

The present invention relates generally to medical devices, and particularly to methods and systems for controlling vibration patterns of a phacoemulsification needle.

BACKGROUND OF THE INVENTION

Various techniques for controlling the vibration pattern of a phacoemulsification needle have been published in the patent literature.

For example, U.S. Pat. No. 10,485,699 describes a phacoemulsification system having a handpiece with a needle. The phacoemulsification system is configured to vibrate the distal end of the needle in both an effective transverse direction and an effective longitudinal direction when power, having a single effective operating frequency is applied to the handpiece.

U.S. Patent Application Publication No. 2017/0027750 describes a phacoemulsification tip including an aspiration tube presenting a cutting tip at a distal end. The aspiration tube has a tube wall presenting an internal face and an external face. The internal face supports at least one internally extending internal ridge. The internal ridge presents an internal distal face, an internal proximal face and an internal apex. The internal distal face meets the internal face at an acute angle measured internally. The internal ridge is structured to engage lens fragments separated from a crystalline lens to enhance proximal movement of the lens fragments and to inhibit distal movement of the lens fragments through the aspiration tube.

U.S. Patent Application Publication No. 2009/0225388 describes a mirror system comprising: a mirror; at least one piezoelectric motor having a coupling surface for coupling the motor to a moveable body; at least one spherical contact surface coupled to the mirror; and a motor mounting frame that holds a piezoelectric motor of the at least one piezoelectric motor and presses the piezoelectric motor coupling surface to a contact surface of the spherical contact surface; wherein the motor is controllable to apply force to the contact surface that rotates the mirror.

SUMMARY OF THE INVENTION

An embodiment of the present invention that is described herein provides a system, including a needle, an actuator assembly and a generator. The needle is configured to be vibrated so as to emulsify a lens of an eye. The actuator assembly, includes a first actuator, a second actuator, and a third actuator, which are distributed around a longitudinal axis of the needle and are configured to vibrate along the longitudinal axis in response to a first driving signal, a second driving signal, and a third driving signal, respectively. The generator is configured to generate the first driving signal, the second driving signal, and the third driving signal, so as to vibrate the needle in accordance with a predefined pattern.

In some embodiments, in vibrating, the first actuator, the second actuator, and the third actuator are configured to deflect the needle from the longitudinal axis in a first direction, a second direction, and a third direction, respectively. In other embodiments, the first actuator, the second actuator and the third actuator are coupled with one another, and the actuator assembly has a toroidal shape, and is coupled with and surrounds a shaft configured to vibrate the needle. In yet other embodiments, the generator is configured to form a three-dimensional (3D) vibration pattern by applying a phase difference between at least two of the first driving signal, the second driving signal, and the third driving signal.

In an embodiment, the generator is configured to generate a first periodic signal having a first frequency and a second periodic signal having a second frequency, and to derive at least one of the first driving signal, the second driving signal and the third driving signal from the first periodic signal and the second periodic signal. In another embodiment, the generator is configured to generate at least one of the first driving signal, the second driving signal, and the third driving signal, by repeatedly applying a sequence including applying the first periodic signal during a first time interval followed by applying the second periodic signal during a second time interval. In yet another embodiment, during the second time interval, the generator is configured to apply the first driving signal with a phase difference relative to the second driving signal.

There is additionally provided, in accordance with an embodiment of the present invention, a system including first, second, and third actuators, a needle and a generator. The first actuator is configured to vibrate along a first axis in response to a first driving signal, the second actuator is configured to vibrate along a second axis, different from the first axis, in response to a second driving signal, and the third actuator is configured to vibrate along a third axis, different from the first axis and the second axis, in response to a third driving signal. The needle is configured to be vibrated by the first actuator, the second actuator, and the third actuator, so as to emulsify a lens of an eye. The generator is configured to generate the first driving signal, the second driving signal, and the third driving signal based on a vibration pattern specified for the needle.

In some embodiments, the first axis, the second axis, and the third axis are orthogonal to one another. In other embodiments, the first actuator, the second actuator, and the third actuator are separated from one another. In yet other embodiments, the generator is configured to vibrate the needle in accordance with a helical pattern, by generating the second driving signal with a defined phase difference relative to the third driving signal.

In an embodiment, the generator is configured to define a step size of the helical pattern by controlling an amplitude of the first driving signal. In another embodiment, the generator is configured to define a diameter size of the helical pattern by controlling an amplitude of at least one of the second driving signal and the third driving signal. In yet another embodiment, the generator is configured to define a shape of the helical pattern by controlling the phase difference between the second driving signal and the third driving signal.

In some embodiments, the generator is configured to define a circular shape for the helical pattern by setting the phase difference to 90 degrees. In other embodiments, the generator is configured to define an elliptical shape for the helical pattern by setting the phase difference to differ from 90 degrees. In yet other embodiments, the generator is configured to vibrate the needle symmetrically with respect to a vibration axis not parallel to a longitudinal axis of the needle.

There is additionally provided, in accordance with an embodiment of the present invention, a method including generating, a first driving signal, a second driving signal, and a third driving signal, for vibrating a needle in accordance with a predefined pattern, so as to emulsify a lens of an eye. The first driving signal is applied to a first actuator, the second driving signal is applied to a second actuator, and the third driving signal is applied to a third actuator, and the first actuator, the second actuator, and the third actuator, are distributed around a longitudinal axis of the needle.

There is further provided, in accordance with an embodiment of the present invention, a method including generating, a first driving signal, a second driving signal, and a third driving signal for vibrating a needle in a vibration pattern specified for emulsifying a lens of an eye. The first driving signal is applied to a first actuator for vibrating the needle along a first axis, the second driving signal is applied to a second actuator for vibrating the needle along a second axis, different from the first axis, and the third driving signal is applied to a third actuator for vibrating the needle along a third axis, different from both the first axis and the second axis.

The present invention will be more fully understood from the following detailed description of the embodiments thereof, taken together with the drawings in which:

DETAILED DESCRIPTION OF EMBODIMENTS

Overview

Embodiments of the present invention that are described hereinafter provide improved techniques for controlling vibration patterns of a phacoemulsification needle applied to a patient's eye undergoing a phacoemulsification procedure, such as a cataract surgery.

In some embodiments, a phacoemulsification system comprises a needle, an actuator assembly and a generator.

The needle is configured to be vibrated so as to emulsify a lens of an eye. The actuator assembly comprises a first actuator, a second actuator and a third actuator, which are distributed around a longitudinal axis of the needle and are configured to vibrate along the longitudinal axis in response to a first driving signal, a second driving signal and a third driving signal, respectively. The generator is configured to generate the first driving signal, the second driving signal and the third driving signal, so as to vibrate the needle in accordance with a predefined pattern.

In some embodiments, the first actuator, the second actuator and the third actuator are coupled with one another, and the actuator assembly has a toroidal shape, and is coupled with and surrounds a shaft configured to vibrate the needle. In some embodiments, the generator is configured to form a three-dimensional (3D) vibration pattern by applying a phase difference between at least two of the first driving signal, the second driving signal and the third driving signal. The generator is further configured to apply an amplitude difference between at least two of the first driving signal, the second driving signal and the third driving signal, so as to form the 3D vibration pattern.

In some embodiments, the generator is configured to generate one or more voltage periodic (e.g., sinusoidal) signal(s) having one or more respective frequencies, and to derive the first, second and third driving signals from the one or more periodic signal(s). The frequency of each periodic signal is selected to achieve resonance in the driven actuators, and is based on various parameters, such as but not limited to the dimensions and material properties of the actuators. For example, when two or more of the actuators are coupled with one another and the generator applies a phase difference and/or an amplitude difference between at least two of the aforementioned driving signals, the resonance frequency may alter.

In some embodiments, the generator is configured to generate at least one of the first driving signal, the second driving signal and the third driving signal, by repeatedly applying a sequence comprising applying the first periodic signal during a first time interval followed by applying the second periodic signal during a second time interval. In such embodiments, the driving signals applied during the first time interval have the same amplitude and do not have phase difference therebetween, so that a vibration axis of the actuator assembly is typically parallel to the longitudinal axis of the needle. However, during the second time interval, the generator is configured to apply the first driving signal with a phase difference relative to the second driving signal, so as to obtain the 3D vibration pattern described above. In general, the generator is configured to determine the vibration pattern of the needle by tuning: (i) the amplitudes of the driving signals, and (ii) when applicable, the phase difference between two or more of the driving signals.

In other embodiments, instead of the actuator assembly described above, the phacoemulsification system may comprise first, second and third actuators, which are disjointed from one another, and are coupled with the shaft in a different configuration. The first actuator is configured to vibrate along a first axis in response to a first driving signal, the second actuator is configured to vibrate along a second axis in response to a second driving signal, and the third actuator is configured to vibrate along a third axis in response to a third driving signal. For example, the first actuator may have a toroidal shape, and is coupled with and surrounds the shaft along the longitudinal axis of the needle. In this configuration, the first axis is typically parallel to the longitudinal axis of the needle. In some embodiments, the first axis, the second axis and the third axis are orthogonal to one another.

In some embodiments, the generator is configured to vibrate the needle in accordance with a helical pattern, by generating the second driving signal with a defined phase difference relative to the third driving signal. The generator is further configured to define: (i) a step size of the helical pattern by controlling an amplitude of the first driving signal, and (ii) a diameter size of the helical pattern by controlling an amplitude of at least one of the second driving signal and the third driving signal.

The disclosed techniques improve the quality of phacoemulsification procedures by providing an eye surgeon with a possibility to apply any suitable vibration pattern of the needle to the patient's eye, e.g., for emulsifying the patient's eye lens during a cataract surgery.

System Description

Figure 1:
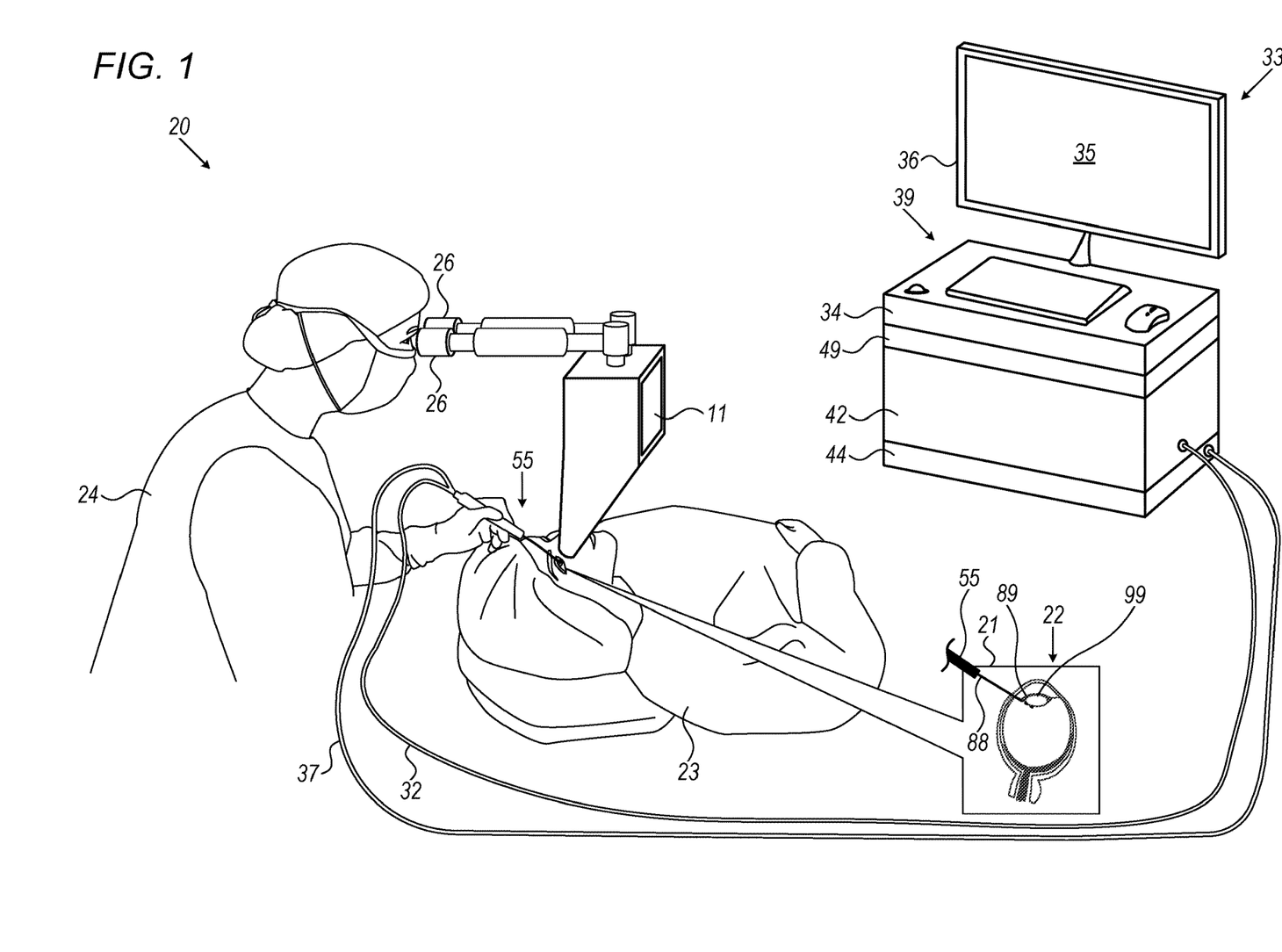
FIG. 1 is a schematic pictorial illustration of an ophthalmic surgical system, in accordance with an embodiment of the present invention.

FIG. 1 is a schematic pictorial illustration of an ophthalmic surgical system 20, in accordance with an embodiment of the present invention. System 20 is configured to carry out various types of ophthalmic procedures, such as but not limited to a cataract surgery.

In some embodiments, system 20 comprises a medical instrument, in the present example a phacoemulsification handpiece, also referred to herein as a tool 55, used by a surgeon 24 to carry out the cataract surgery. In other embodiments, system 20 may comprise other surgical tools, such as but not limited to an irrigation and aspiration (I/A) handpiece, a diathermy handpiece, a vitrectomy handpiece, and similar instruments.

Reference is now made to an inset 21 showing a sectional view of the surgical procedure carried out in an eye 22 of a patient 23. In some embodiments, surgeon 24 applies tool 55 for treating eye 22, and in the present example, surgeon 24 inserts a needle 88 of tool 55 into eye 22. In the example of inset 21, during a cataract surgical procedure, surgeon 24 inserts needle 88 into capsular bag 89 so as to emulsify a lens 99 of eye 22.

Reference is now made back to the general view of FIG. 1. In some embodiments, system 20 comprises a console 33, which comprises a processor 34, a memory 49, a generator 44 and a cartridge 42. In some embodiments, cartridge 42 comprises pumping sub-systems (not shown) configured to apply, via multiple tubes 32, irrigation fluids (not shown) into eye 22 and to draw eye fluids away from eye 22 into cartridge 42. In the context of the present invention, the term "eye fluid" refers to any mixture of natural eye fluid, irrigation fluid and lens material. Note that tubes 32 may comprise an irrigation tube for supplying the irrigation fluid into eye 22, and a separate aspiration tube for drawing the eye fluids away from eye 22.

In some embodiments, generator 44 is electrically connected to tool 55, via a plurality of wires (shown in FIG. 3 below) referred to herein as an electrical cable 37. Generator 44 is configured to generate one or more voltage periodic (e.g., sinusoidal) signals, also referred to herein as periodic signals, having one or more frequencies, respectively. Generator 44 is further configured to generate a plurality of driving signals, so as to vibrate needle 88 of tool 55 in accordance with a predefined pattern, so as to emulsify lens 99 of eye 22. Embodiments related to the periodic signals and driving signals are described in detail in FIGS. 2-5 below.

In some embodiments, processor 34 typically comprises a general-purpose computer, with suitable front end and interface circuits for controlling generator 44, cartridge 42 and other components of system 20.

In some embodiments, system 20 comprises an ophthalmic surgical microscope 11, such as ZEISS OPMI LUMERA series or ZEISS ARTEVO series supplied by Carl Zeiss Meditec AG (Oberkochen, Germany), or any other suitable type of ophthalmic surgical microscope provided by other suppliers. Ophthalmic surgical microscope 11 is configured to produce stereoscopic optical images and two-dimensional (2D) optical images of eye 22. During the cataract surgery, surgeon 24 typically looks though eyepieces 26 of ophthalmic surgical microscope 11 for viewing eye 22.

In some embodiments, console 33 comprises a display 36 and other input device 39, which may be used by surgeon 24 for controlling tool 55 and other components of system 20. Moreover, processor 34 is configured to display on display 36, an image 35 received from any suitable medical imaging system for assisting surgeon to carry out the cataract surgery.

This particular configuration of system 20 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of ophthalmic and other minimally invasive and surgical systems.

Figure 2:
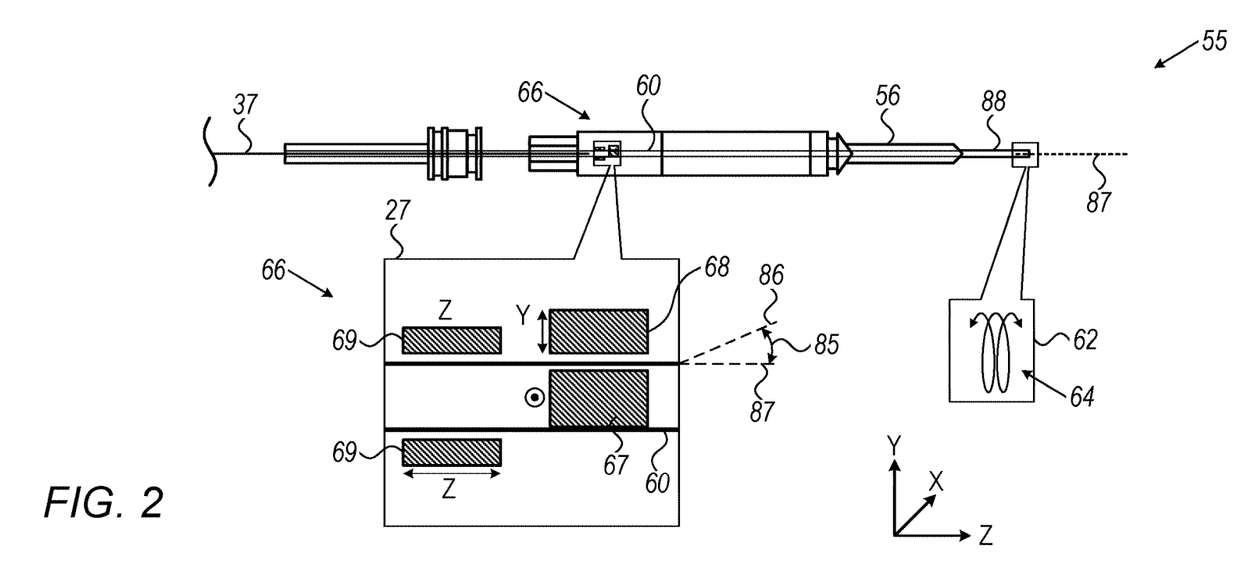
FIG. 2 is a schematic pictorial illustration of a phacoemulsification handpiece, in accordance with an embodiment of the present invention.

Vibrating a Needle of a Phacoemulsification Handpiece in Accordance with a Predefined Pattern to Carry Out a Cataract Surgery FIG. 2 is a schematic pictorial illustration of tool 55, in accordance with an embodiment of the present invention. In some embodiments, tool 55 comprises needle 88 and a coaxial irrigation sleeve 56 that at least partially surrounds needle 88 and creates a fluid pathway between the external wall of the needle and the internal wall of the irrigation sleeve. Note that needle 88 is hollow, and is configured to aspirate fluids from the patient's eye, along a longitudinal axis 87 of the needle, during the cataract surgery. In the present example, needle 88 is configured to draw at least eye fluid (e.g., natural eye fluid, irrigation fluid and lens material) from the patient's eye through the aspiration tube described in FIG. 1 above.

In other embodiments, needle 88 or another suitable element of tool 55 may be able to transfer irrigation fluid from the irrigation tube (described in FIG. 1 above) to the patient's eye.

In some embodiments, tool 55 comprises an actuator assembly 66 comprising multiple actuators, in the present example three actuators 67, 68 and 69 made from piezoelectric crystals and coupled with a shaft 60, for driving vibration of needle 88. The piezoelectric crystals are configured to vibrate needle 88 in a resonant vibration mode in response to receiving, via cable 37, driving signals from generator 42. The vibration of needle 88 is used for breaking the cataract of the patient's eye into small pieces, e.g., constitutes the aforementioned lens material, during the phacoemulsification procedure.

Reference is now made to an inset 27 showing actuator assembly 66. In some embodiments, actuators 67-69 are placed in contact with shaft 60. In the example of FIG. 2, actuator 69 has a toroidal shape surrounding and coupled with shaft 60. Actuator 69 is configured, in response to receiving a driving signal also referred to herein as a first driving signal, to vibrate along a Z-axis of an XYZ coordinate system.

In the context of the present invention and in the claims, the terms "first driving signal," "second driving signal" and "third driving signal" refer to similar or different driving signals, which are applied to actuators 69, 68 and 67, respectively, and are indexed using the terms "first," "second" and "third."

In some embodiments, actuator 68 is coupled with shaft 60 and is configured, in response to receiving the second driving signal, to vibrate along a Y-axis of the XYZ coordinate system. Similarly, actuator 67 is coupled with shaft 60 and configured, in response to receiving the third driving signal, to vibrate along an X-axis of the XYZ coordinate system.

In some embodiments, generator 44 is configured to vibrate needle 88 in accordance with a predefined pattern. In the example of FIG. 2, generator 44 is configured to apply voltage signals of the aforementioned first, second and third driving signals having a frequency range between about 26 KHz and 130 KHz, with a preferred frequency of about 40 KHz, e.g. 39.4 KHz. When applying the first driving signal to actuator 69, actuator assembly 66 generates a vibration (back and forth) in Z-axis, so that the vibration generated by actuator assembly 66 is typically parallel to longitudinal axis 87 of needle 88.

In some embodiments, when applying the first, second and third driving signals to actuators 69, 68 and 67, respectively, a vibration axis 86 may have an angle 85 relative to longitudinal axis 87, in the XYZ space, as shown in inset 27.

In some embodiments, generator 44 is further configured to apply at least two of the driving signals with a phase difference. For example, generator 44 is configured to generate a circular shape of a vibration pattern in an XY plane, by applying to actuators 68 and 67 the respective second and third driving signals, with a phase difference of 90°. Moreover, when generating the circular shape of the vibration pattern, generator 44 is configured to define the diameter size of a circular vibration of needle 88 by controlling the amplitude of the second driving signal and the third driving signal applied to actuators 68 and 67, respectively.

In other embodiments, generator 44 is configured to define an elliptical shape of the needle vibration, by setting the phase difference to differ from 90°. In such embodiments, generator 44 is configured to define the size of the long and short axes of the ellipse, by controlling the amplitude of the second driving signal and the third driving signal applied to actuators 68 and 67, respectively.

Reference is now made to an inset 62 showing the vibration pattern of needle 88 in response to the driving signals supplied by generator 44. In an embodiment, generator 44 is configured to generate a helical pattern 64 of needle 88 by combining the circular shape of vibration pattern in XY plane, as described above, with a linear vibration in Z-axis, which is produced by applying the first driving signal to actuator 69. Note that the amplitude of each driving signal is indicative of the vibration range. For example, generator 44 is configured to control the step (along Z-axis) of helical pattern 64, by controlling the voltage amplitude of the first driving signal.

Reference is now made back to inset 27, by controlling the amplitude of the second and third driving signals, without applying a phase difference between driving signals, generator 44 is configured to control angle 85 between vibration axis 86 and longitudinal axis 87 of needle 88. In some embodiments, generator 44 is configured to vibrate needle 88 symmetrically with respect to vibration axis 86, which is not parallel to longitudinal axis 87. For example, generator 44 is configured to generate an angle of 45° in XY plane, between axes 86 and 87 by applying the same voltage amplitude to actuators 67 and 68.

Note that the frequency of the driving signals is determined for obtaining resonance in the driven actuators, and is based on various parameters, such as the structure of the actuators (e.g., piezoelectric) material, the size of the actuators, and interactions between elements of the actuator assembly and other elements, such as shaft 60.

This particular configuration of tool 55 and actuator assembly 66 are simplified and shown by way of example, in order to illustrate certain problems that are addressed by embodiments of the present invention and to demonstrate the application of these embodiments in enhancing the performance of such a phacoemulsification system. Embodiments of the present invention, however, are by no means limited to this specific sort of example phacoemulsification handpiece and actuator assembly, and the principles described herein may similarly be applied to other sorts of phacoemulsification handpieces and actuator assemblies used in ophthalmic surgical systems.

Figure 3:
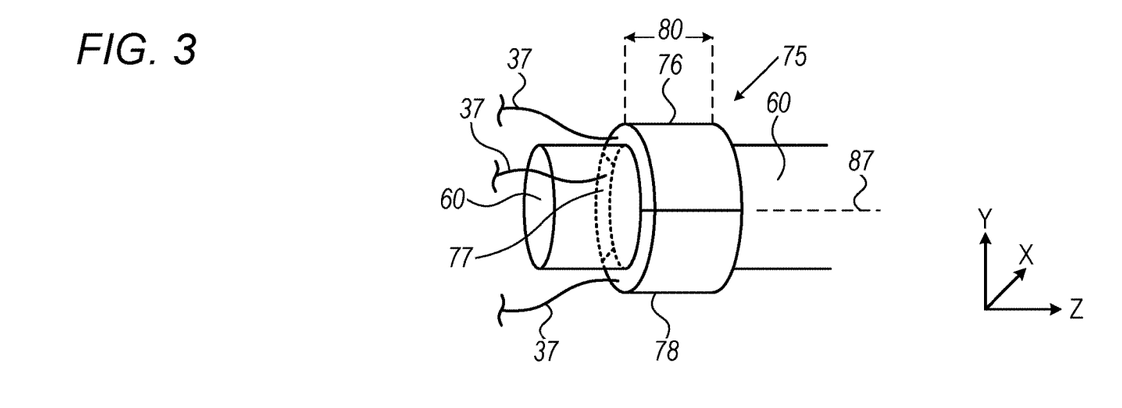
FIG. 3 is a schematic pictorial illustration of an actuator assembly of a phacoemulsification handpiece, in accordance with another embodiment of the present invention.

FIG. 3 is a schematic pictorial illustration of an actuator assembly 75 of a phacoemulsification handpiece, in accordance with another embodiment of the present invention. Actuator assembly 75 may replace, for example, actuator assembly 66 of FIG. 2 above.

In some embodiments, actuator assembly 75 comprises three actuators 76, 77 and 78, which are coupled with one another and are arranged in a toroidal shape. In the present example, actuators 76-78 are made from any suitable type of piezoelectric materials, e.g., piezoelectric materials similar to that of actuators 67-69 described in FIG. 2 above.

In some embodiments, actuator assembly 75 is coupled with and surrounds shaft 60 at any suitable position along the Z-axis of shaft 60. Actuator assembly 75 has a size 80 (e.g., between about 10 mm and 60 mm) in Z-axis, typically, but not necessarily, similar to all actuators 76, 77 and 78.

In some embodiments, actuators 76, 77 and 78 are configured to receive from generator 44, first, second and third driving signals, respectively, using the same techniques described in FIGS. 1 and 2 above. In in vibrating, actuators 76, 77 and 78 are configured to deflect needle 88 from longitudinal axis 87 of needle 88 in a first direction, a second direction and a third direction, respectively. The first, second and third directions are determined by the first, second and third driving signals, respectively, as described herein.

In some embodiments, generator 44 is configured to apply a voltage signal having the same frequency (e.g., about 40 KHz) and same amplitude, to actuators 76, 77 and 78 in the first, second and third driving signals, respectively.

In some embodiments, in response to the driving signals, actuators 76-78 of actuator assembly 75 are configured to lengthen and shorten mutually and evenly along Z-axis, and thereby, to vibrate needle solely in Z-axis.

In some embodiments, generator 44 is configured to form a three-dimensional (3D) vibration pattern by applying a phase difference between at least two of the first driving signal, the second driving signal and the third driving signal. For example, generator 44 is configured to generate the first, second and third driving signals with (i) the same frequency and amplitude, (ii) without phase difference between the first and second, and (iii) with a phase difference (e.g., of 180°) between the second and third driving signals. In such embodiments, actuator assembly 75 is configured to oscillate in the XYZ space because actuators 76 and 77 elongate and actuator 78 shortens at the same time. For example, in response to a phase difference between at least two of the driving signals applied to actuators 76-78, the resonance frequency in actuators 76-78 of actuator assembly 75 may be altered from about 40 KHz to about 27 KHz. The different resonance frequency may be caused by a difference in the intrinsic mechanical resistance of actuator assembly 75, for the movement described above, or from any other reason. Note that the resonance frequencies of about 40 KHz and 27 KHz are provided by way of example, and in other embodiments, the actuators of actuator assemblies 66 and 75 may have any other suitable resonance frequencies determined by the dimensions and material of the actuators.

In some embodiments, generator 44 is configured to derive at least one of the first, second and third driving signals from a combination of two periodic signals. In the present example, generator 44 is configured to generate a sequence of two voltage sinusoidal signals, wherein one of the signals has a first frequency, e.g., between about 26 kHz and 130 KHz, preferably a frequency of about 40 KHz, e.g. 39.4 KHz. The other signal has a second, different frequency, e.g., between about 17 KHz and 80 KHz, and preferably a frequency of about 27 KHz or any other suitable frequency within this range. Note that the frequency used in the driving signals can be identical or about the same for the first, second and third driving signals, depending on the required vibration pattern. In such embodiments, at a first time interval, generator 44 is configured to apply the same driving signal having a frequency of about 40 KHz (or any other suitable frequency selected within the range between about 26 kHz and 130 KHz described above) to all of actuators 76-78. This means that in this case no phase difference exists between the driving signals applied to the actuators. Note that when the vibration is required to be precisely parallel to axis 87, it is important to apply the same frequency and amplitude to all of actuators 76-78, without phase difference between the first, second and third driving signals. At a second, different, time interval, generator 44 is configured to apply the driving signal having a frequency of about 27 KHz, e.g. 18.8 KHz, or any other suitable frequency selected within the range between about 17 kHz and 80 KHz described above, to actuators 76-78, wherein in this case a suitable phase difference (e.g., of 180°) exists between any pair of driving signals applied to actuators 76-78 (e.g., between driving signals applied to actuators 76 and 77). Generator 44 is further configured to generate at least one of the first, second and third driving signal, by repeatedly applying a sequence comprising applying the driving signal having a frequency of about 40 KHz during a first time interval followed by applying the driving signal having a frequency of about 27 KHz during a second time interval.

In some embodiments, generator 44 is configured to set different amplitudes to at least two of the first, second and third driving signals. In such embodiments, similarly to the description above, in response to the driving signals having a frequency of about 40 KHz, actuator assembly 75 vibrates along Z-axis, and in response to the driving signals having a frequency of about 27 KHz (having an appropriate phase difference), actuator assembly 75 vibrates needle 88 in a three-dimensional (3D) vibration pattern.

In some embodiments, using the techniques described above, generator 44 is configured to cause needle 88 to vibrate in accordance with any desired vibration pattern. The vibration pattern is achieved by applying the first, second and third driving signals to actuators 76, 77 and 78, respectively, using a suitable combination of the driving signal having a frequency of about 40 KHz and the driving signal having a frequency of about 27 KHz with selected phase differences and/or amplitude differences among the first, second and third driving signals.

In alternative embodiments, actuators 76, 77 and 78 are distributed around longitudinal axis 87 of needle 88 without being coupled with one another. In such embodiments, actuators 76, 77 and 78 are still configured to vibrate along vibration axis 86 in response to the first, second and third driving signals, respectively, as described above. Additionally, or alternatively, at least two of actuators 76, 77 and 78 may be coupled with one another using any suitable connecting element made from any suitable material and having any suitable geometry.

In other embodiments, actuators 76-78 are coupled with one another and are mutually arranged such that actuator assembly 75 has a solid cylindrical shape. In such embodiments, actuator assembly 75 is coupled with the proximal end of shaft 60, so as to vibrate needle 88 in accordance with any suitable predefined pattern using the techniques described above. In yet other embodiments, actuator assembly 75 may have any other suitable shape configured for vibrating needle 88 in accordance with any suitable pattern. In such embodiments, tool 55 may have any other suitable configuration (in addition to or instead of shaft 60) for transmitting the aforementioned vibrations to needle 88.

In yet alternative embodiments, actuator assembly 75 may comprise any suitable number of actuators, wherein at least some of them are coupled together.

Figure 4:
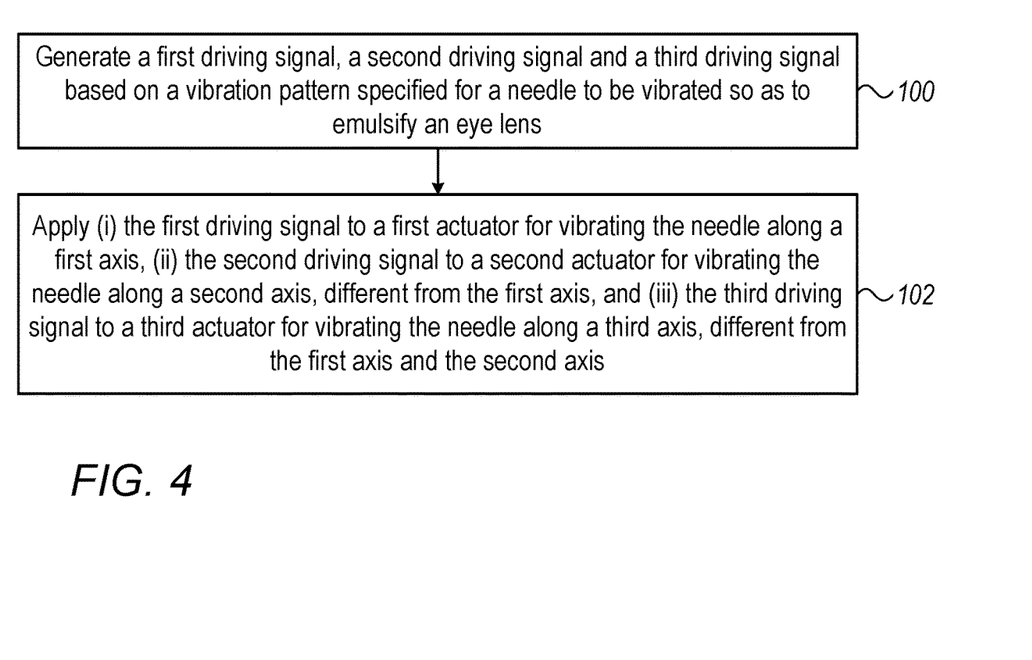
FIGS. 4 and 5 are flow chart that schematically illustrate methods for emulsifying a lens of an eye by vibrating a needle using a predefined pattern, in accordance with embodiments of the present invention.

FIG. 4 is a flow chart that schematically illustrates a method for emulsifying lens 99 of eye 22 by vibrating needle 88 using a predefined pattern, in accordance with an embodiment of the present invention.

The method begins at a driving signal generation step 100, with generating, e.g., using generator 44, a first driving signal, a second driving signal and a third driving signal. As described in FIG. 2 above, the first, second and third driving signals have a first frequency (e.g., between about 27 KHz and 130 KHz, with a preferred selected frequency of about 40 KHz) and are generated based on a vibration pattern specified for needle 88 to be vibrated so as to emulsify lens 99 of eye 22.

At a driving signal applying step 102 that concludes the method, generator 44 applies: (i) the first driving signal to actuator 69 for vibrating needle 88 along Z-axis, (ii) the second driving signal to actuator 68 for vibrating needle 88 along Y-axis, and (iii) the third driving signal to actuator 67 for vibrating needle 88 along X-axis.

In some embodiments, generator 44 is configured to control a phase difference of about 90° between the second driving signal and the third driving signal, so as define a circular shape for a helical vibration pattern applied to needle 88, as described in FIG. 2 above.

Figure 5:
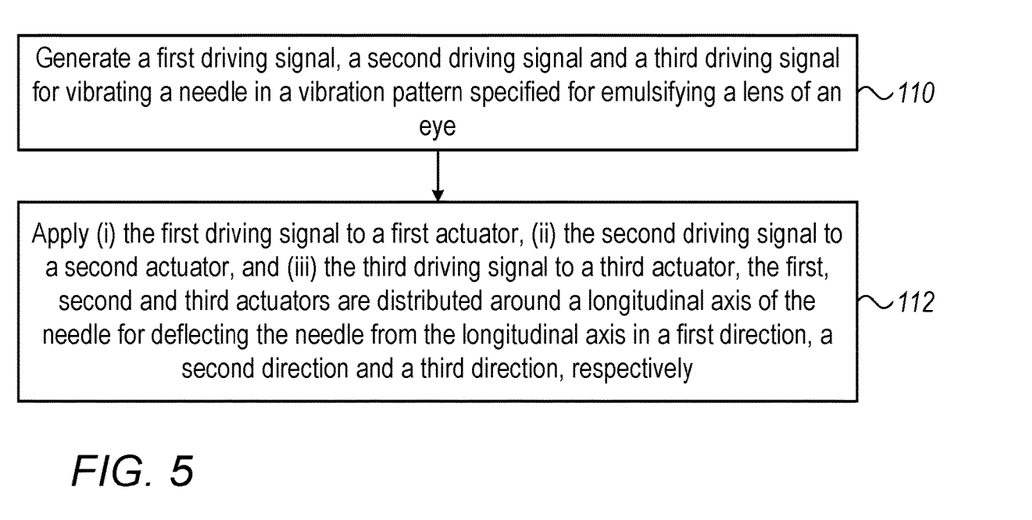

FIG. 5 is a flow chart that schematically illustrates a method for emulsifying lens 99 of eye 22 by vibrating needle 88 using a predefined pattern, in accordance with another embodiment of the present invention.

The method begins at a driving signal generation step 110, with generating, e.g., using generator 44, a first driving signal, a second driving signal and a third driving signal for vibrating needle 88 in a vibration pattern specified for emulsifying lens 99 of eye 22.

In some embodiments that are described in FIG. 3 above, generator 44 generates a first periodic signal having a first frequency (e.g., between about 27 KHz and 130 KHz, with a preferred selected frequency of about 40 KHz) and a second periodic signal having a second frequency (e.g., between about 17 KHz and 80 KHz, with a preferred selected frequency of about 27 KHz), and derives at least one of the first driving signal, the second driving signal and the third driving signal from the first periodic signal and the second periodic signal. Generator 44 generates at least one of the first driving signal, the second driving signal and the third driving signal, by repeatedly applying a sequence comprising applying the first periodic signal during a first time interval followed by applying the second periodic signal during a second time interval.

At a driving signal applying step 112 that concludes the method, generator 44 applies: (i) the first driving signal to actuator 76, (ii) the second driving signal to actuator 77, and (iii) the third driving signal to actuator 78. As shown in FIG. 3 above, actuators 76-78 are distributed around longitudinal axis 87 of needle 88 for deflecting the needle from longitudinal axis 88 in a first direction, a second direction and a third direction, respectively. In some embodiments, during the second time interval, generator 44 may apply the first driving signal with a phase difference relative to the second driving signal so as to obtain the specified vibration pattern, as described in detail in FIG. 3 above. Moreover, generator 44 may set different amplitudes to at least two of the first, second and third driving signals, so as to obtain the specified vibration pattern.

Although the embodiments described herein mainly address controlling vibration patterns of a phacoemulsification needle applied in a cataract surgery, the methods and systems described herein can also be used in other applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
a first actuator, which is configured to vibrate along a first axis in response to a first driving signal;
a second actuator, which is configured to vibrate along a second axis, different from the first axis, in response to a second driving signal;
a third actuator, which is configured to vibrate along a third axis, different from the first axis and the second axis, in response to a third driving signal;
wherein the first axis, the second axis and the third axis are orthogonal to one another;
a needle, which is configured to be vibrated by the first actuator, the second actuator and the third actuator, so as to emulsify a lens of an eye; and
a generator, which is configured to generate the first driving signal, the second driving signal and the third driving signal based on a vibration pattern specified for the needle.

2. The system according to claim 1, wherein the first actuator, the second actuator and the third actuator are separated from one another.

3. The system according to claim 1, wherein the generator is configured to vibrate the needle in accordance with a helical pattern, by generating the second driving signal with a defined phase difference relative to the third driving signal.

4. The system according to claim 3, wherein the generator is configured to define a step size of the helical pattern by controlling an amplitude of the first driving signal.

5. The system according to claim 3, wherein the generator is configured to define a diameter size of the helical pattern by controlling an amplitude of at least one of the second driving signal and the third driving signal.

6. The system according to claim 3, wherein the generator is configured to define a shape of the helical pattern by controlling the phase difference between the second driving signal and the third driving signal.

7. The system according to claim 6, wherein the generator is configured to define a circular shape for the helical pattern by setting the phase difference between the second driving signal and the third driving signal to 90 degrees.

8. The system according to claim 6, wherein the generator is configured to define an elliptical shape for the helical pattern by setting the phase difference between the second driving signal and the third driving signal to differ from 90 degrees.

9. The system according to claim 1, wherein the generator is configured to vibrate the needle symmetrically with respect to a vibration axis not parallel to a longitudinal axis of the needle.

10. A method, comprising:
generating, a first driving signal, a second driving signal and a third driving signal for vibrating a needle in a vibration pattern specified for emulsifying a lens of an eye; and
applying, (i) the first driving signal to a first actuator for vibrating the needle along a first axis, (ii) the second driving signal to a second actuator for vibrating the needle along a second axis, different from the first axis, and (iii) the third driving signal to a third actuator for vibrating the needle along a third axis, different from both the first axis and the second axis, wherein the first axis, the second axis, and the third axis are orthogonal to one another.

11. The method according to claim 10, wherein the first actuator, the second actuator, and the third actuator are separated from one another.

12. The method according to claim 10, wherein vibrating the needle comprises vibrating the needle in accordance with a helical pattern, by generating the second driving signal with a defined phase difference relative to the third driving signal.

13. The method according to claim 12, wherein generating the first driving signal, the second driving signal and the third driving signal comprises, defining a step size of the helical pattern by controlling an amplitude of the first driving signal.

14. The method according to claim 12, wherein generating the first driving signal, the second driving signal and the third driving signal comprises, defining a diameter size of the helical pattern by controlling an amplitude of at least one of the second driving signal and the third driving signal.

15. The method according to claim 12, wherein vibrating the needle comprises defining a shape of the helical pattern by controlling the phase difference between the second driving signal and the third driving signal.

16. The method according to claim 15, wherein vibrating the needle comprises defining a circular shape for the helical pattern by setting the phase difference between the second driving signal and the third driving signal to 90 degrees.

17. The method according to claim 15, wherein vibrating the needle comprises defining an elliptical shape for the helical pattern by setting the phase difference between the second driving signal and the third driving signal to differ from 90 degrees.

18. The method according to claim 10, wherein vibrating the needle comprises vibrating the needle symmetrically with respect to a vibration axis not parallel to a longitudinal axis of the needle.

* * * * *